US007390339B1

(12) United States Patent
Warrick et al.

(10) Patent No.: US 7,390,339 B1
(45) Date of Patent: Jun. 24, 2008

(54) VORTEX SEPARATOR IN PARTICLE DETECTION SYSTEMS

(75) Inventors: Bret R. Warrick, Grants Pass, OR (US); Ivan K. Horban, Grants Pass, OR (US); Michael M. Carrabba, Rogue River, OR (US)

(73) Assignee: Hach Ultra Analytics, Inc., Grants Pass, OR (US)

( * ) Notice: Subject to any disclaimer, the term of this patent is extended or adjusted under 35 U.S.C. 154(b) by 530 days.

(21) Appl. No.: 11/122,408

(22) Filed: May 5, 2005

(51) Int. Cl.
*B01D 45/12* (2006.01)

(52) U.S. Cl. ............................ 55/346; 55/349; 55/431; 55/459.1; 96/413; 96/417

(58) Field of Classification Search .................. 55/343, 55/346, 349, 459.1, 430, 431; 96/417, 430, 96/431, 413; 73/31.03, 31.02, 31.07
See application file for complete search history.

(56) References Cited

U.S. PATENT DOCUMENTS

| | | | | |
|---|---|---|---|---|
| 840,301 | A | 1/1907 | Cook | |
| 2,236,548 | A | 4/1941 | Prouty | |
| 3,318,070 | A | 5/1967 | Zeiss et al. | |
| 3,885,933 | A | 5/1975 | Putney | 55/397 |
| 4,486,207 | A | 12/1984 | Baillie | 55/455 |
| 4,588,558 | A | 5/1986 | Kam et al. | 422/113 |
| 4,624,772 | A | 11/1986 | Krambeck et al. | 208/95 |
| 4,670,410 | A | 6/1987 | Baillie | 502/41 |
| 4,714,541 | A | 12/1987 | Buyan et al. | 208/161 |
| 5,417,931 | A | 5/1995 | Cetinkaya | 422/139 |
| 6,111,642 | A | 8/2000 | DeFreez et al. | 357/337 |
| 6,156,212 | A | 12/2000 | Rader et al. | 210/788 |
| 6,193,075 | B1 | 2/2001 | Plas | 209/715 |
| 6,217,636 | B1 * | 4/2001 | McFarland | 95/216 |
| 6,695,146 | B2 | 2/2004 | Call et al. | 209/143 |
| 6,746,500 | B1 * | 6/2004 | Park et al. | 55/343 |
| 6,777,228 | B2 | 8/2004 | Lejeune | 435/309 |
| 6,846,463 | B1 | 1/2005 | Dries et al. | 422/147 |
| 6,887,710 | B2 | 5/2005 | Call et al. | 436/53 |
| 2004/0010379 | A1 | 1/2004 | Craig et al. | 702/22 |
| 2004/0208801 | A1 | 10/2004 | Huziwara et al. | 422/147 |
| 2004/0232052 | A1 | 11/2004 | Call et al. | 209/143 |
| 2005/0070025 | A1 | 3/2005 | Mooradian et al. | 436/178 |
| 2005/0073683 | A1 | 4/2005 | Gard et al. | 356/337 |

OTHER PUBLICATIONS

Chen, et al.; "Performance of a TSI Aerodynamic Particle Sizer", Aerosol Sci & Tech. 4:89-97 (1985).

(Continued)

*Primary Examiner*—Robert A Hopkins
(74) *Attorney, Agent, or Firm*—Stoel Rives LLP; Matthew S. Bethards

(57) ABSTRACT

A particle separation apparatus is disclosed. The particle separation apparatus may be for sample air stream preparation and delivery in particle detection systems. The particle separation apparatus may include a first vortex separator coupled to a second vortex separator for selecting particles in the air stream that are within a desirable size range for particle detection. The second vortex separator may further increase the concentration of particles within the desirable size range per unit volume. The particle separation apparatus may deliver the size-selected air stream to a detector, such as a laser-induced fluorescence detection system.

25 Claims, 7 Drawing Sheets

OTHER PUBLICATIONS

Luoma, et al., "A Fluorescence Particle Detector for Real Time Quantification of Viable Organisms in Air", Proceeding of SPIE, vol. 4576 (2002).

Mesosystems, Micro Vic Particle Concentrator (2004).

National Research Council, Sensor Systems for Biological Attach Atgents (2005) National Academies Press, Washington DC (Chpt. 4-5).

* cited by examiner

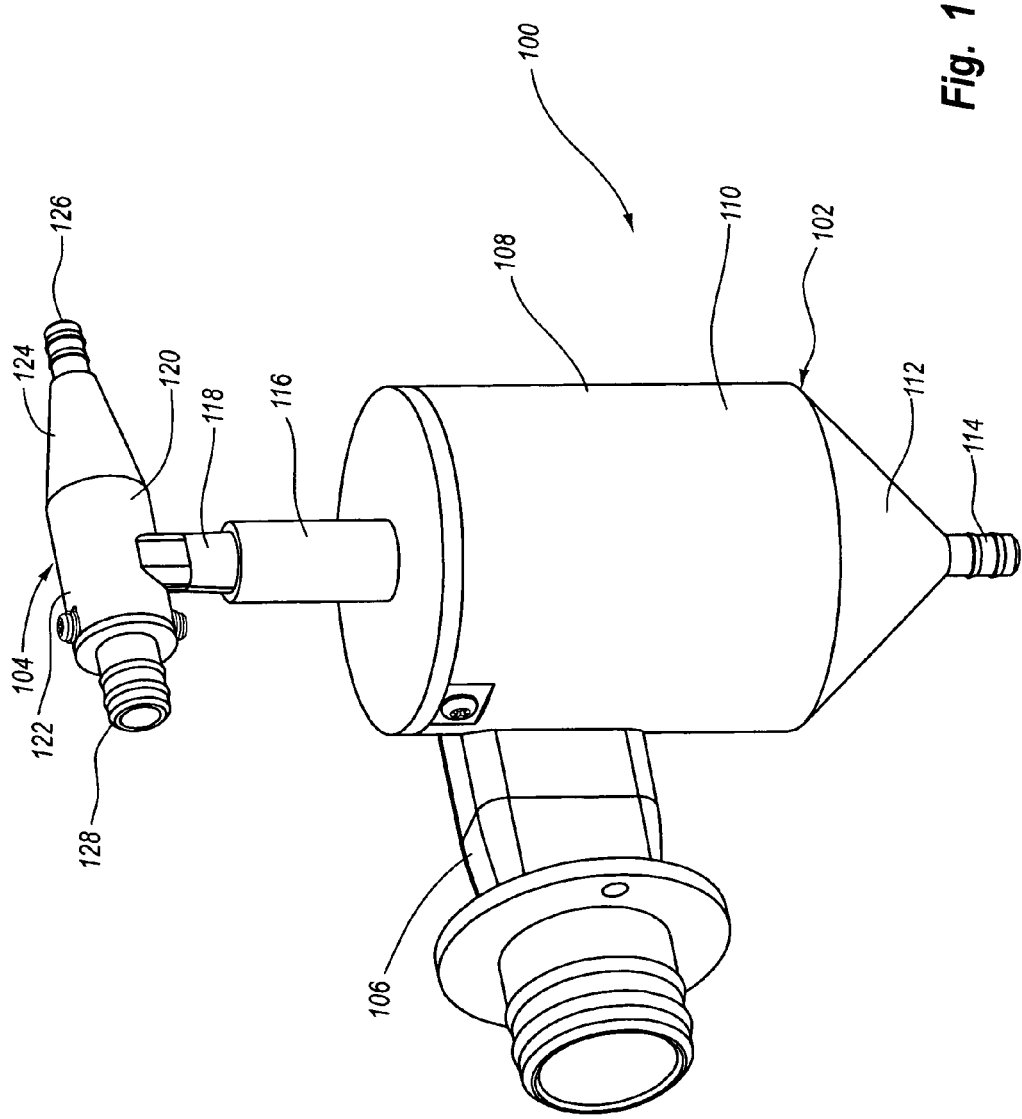

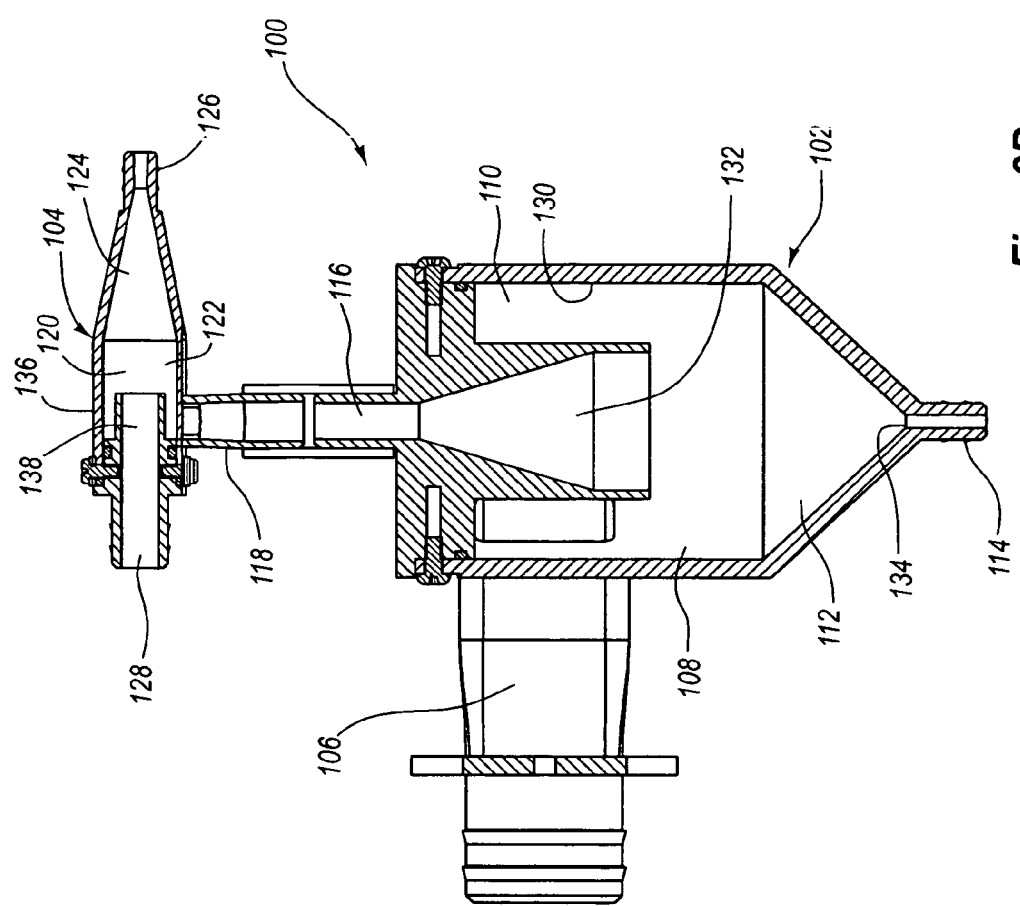
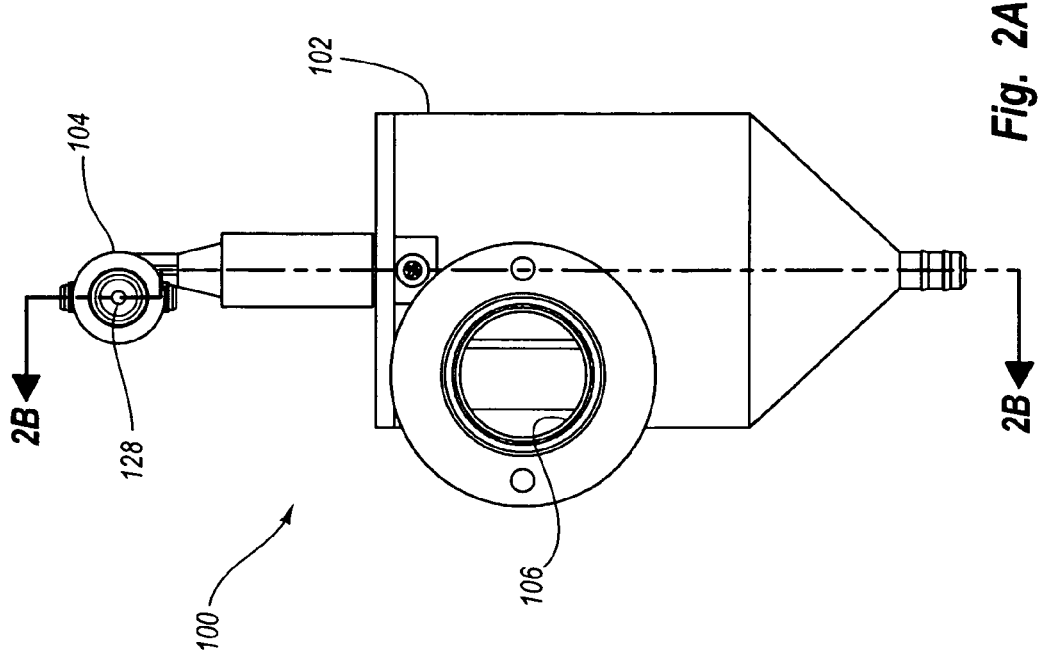
Fig. 2B
Fig. 2A

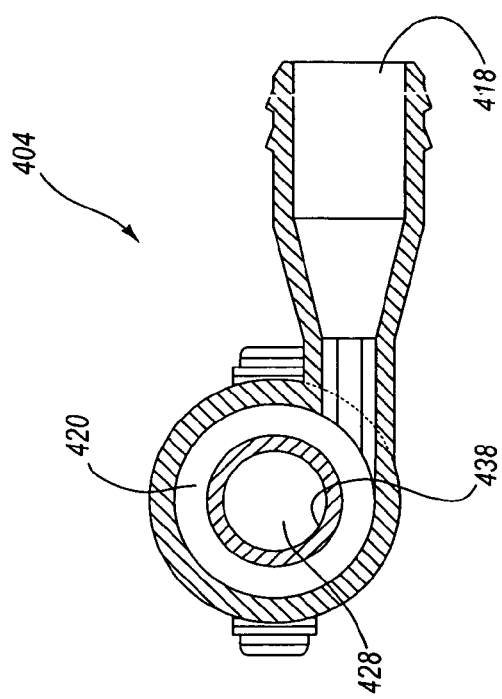
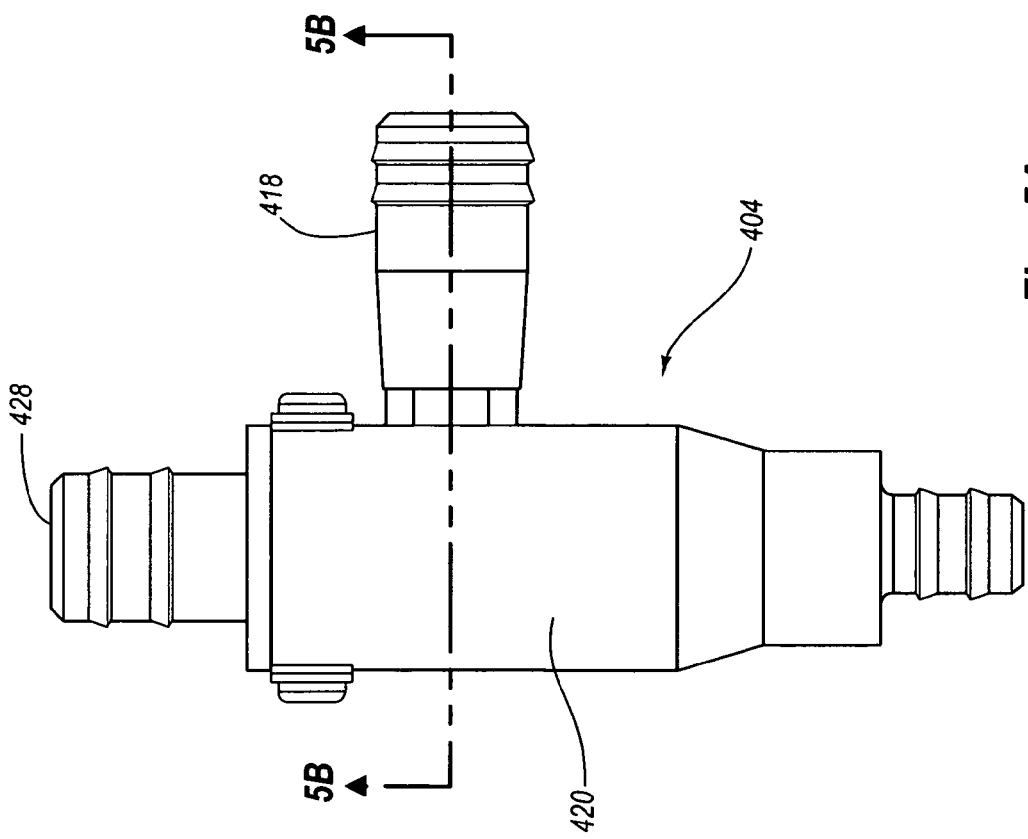
Fig. 5B
Fig. 5A ns or death.

VORTEX SEPARATOR IN PARTICLE DETECTION SYSTEMS

BACKGROUND

Contamination control, including particulate monitoring, plays a role in the manufacturing processes of several industries. These industries require clean rooms or clean zones with active air filtration and require the supply of clean raw materials such as process gases, de-ionized water, chemicals, and substrates. In the pharmaceutical industry, the Food and Drug Administration requires particulate monitoring because of the correlation between detected particles in an aseptic environment and viable particles that contaminate the product produced.

Recent attention has been given to the monitoring and detection of biological agents. If aerosolized agents (biological particles) are introduced into an environment and are within the respirable range of particle sizes, then the biological particles may deposit in human lungs resulting in illness or death.

Biological contamination can occur not only in open air, but also in confined spaces, such as postal handling equipment, aircraft, hospitals, water supplies, and air ducts. Minimizing the introduction of biological particles in an environment requires the fast detection of pathogens. Laser-induced fluorescence ("LIF") of fluorescent biological substances (biofluorophores) provides a real-time technique for identifying the potential presence of airborne pathogens such as aerosolized bacterial spores and viruses. Biofluorophores significant to LIF include, but are not limited to, tryptophan, NADH, and riboflavin or other flavinoids.

Assemblies that have been used in sample preparation for detection of particles include pre-filter scalpers and concentrators. A scalper may be a device used to separate out particles in the sample air stream, for example, based on particle size. A concentrator may be used to increase particle concentration by increasing the number of particles by volume in the sample air stream.

One category of scalpers that has been used to separate out large particles from particle-laden air streams is vortex separators, also known as cyclone separators. A classical vortex separator device has a settling chamber in the form of a cylinder. The particle-laden air sample enters the cylinder tangentially and spirals downward in the chamber in a vortex due to the pressure distribution in the chamber and chamber geometry. As the particle-laden air stream travels around the vortex, the larger particles are pushed toward the chamber walls due to centrifugal forces. Below the cylindrical portion of the chamber is a conical section, which causes the vortex diameter to decrease until the majority of the spinning air stream spins up the center of the chamber in an inner vortex to the vortex finder. The smaller particles, having less mass, get caught in the suction of the inner vortex that exits the vortex finder. Larger particles that are centrifuged to the wall of the chamber are not part of the sample that exits the vortex finder.

SUMMARY

Exemplary embodiments of particle separation devices are disclosed. According to one embodiment, a particle separation apparatus having two vortex separators is provided. The two vortex separators may provide particles that are within a desirable size range to a particle detection system.

According to an alternative embodiment one of the two vortex separators may also increase the concentration of particles that are within the desirable size range. Furthermore, another embodiment may include an eductor coupled to a minor flow outlet of the first vortex separator. For instance, the eductor may be a venturi tube.

According to another alternative embodiment, the particle separation apparatus may include a third vortex separator, and alternatively a fourth vortex separator. The combination of vortex separators may be to select and concentrate particles that are within the desirable size range. Moreover, the vortex separators may also be configured to concentrate particles that are within the desirable size range for deposition onto a substrate for particle analysis.

Another alternative embodiment of a particle separation apparatus may include a vortex separator and a concentrator device for selecting particles within a desirable size range and increasing their concentration for delivery to a particle detector. The vortex separator and concentrator device may be disposed within a housing of a particle detection system. The concentrator device may be a second vortex separator. Alternatively, the concentrator device may be a virtual impactor.

BRIEF DESCRIPTION OF THE DRAWINGS

The present embodiments will become more fully apparent from the following description and appended claims, taken in conjunction with the accompanying drawings. Understanding that these drawings depict only typical embodiments and are, therefore, not to be considered limiting of the invention's the embodiments will be described with additional specificity and detail use of the accompanying drawings in which:

FIG. 1 is a perspective view of one embodiment of a particle separation apparatus having first and second stage vortex separators;

FIG. 2A is a side elevation view of the particle separation apparatus of FIG. 1;

FIG. 2B is a side cross sectional view of the particle separation apparatus of FIG. 2A as viewed along the cross-sectional plane 2B-2B;

FIG. 5A is a side elevation view of a second stage vortex separator that is part of a particle separation apparatus;

FIG. 5B is a cross sectional plan view of the second stage vortex separator of FIG. 5A as viewed along the cross-sectional plane 5B-5B;

DETAILED DESCRIPTION

Figure 3:
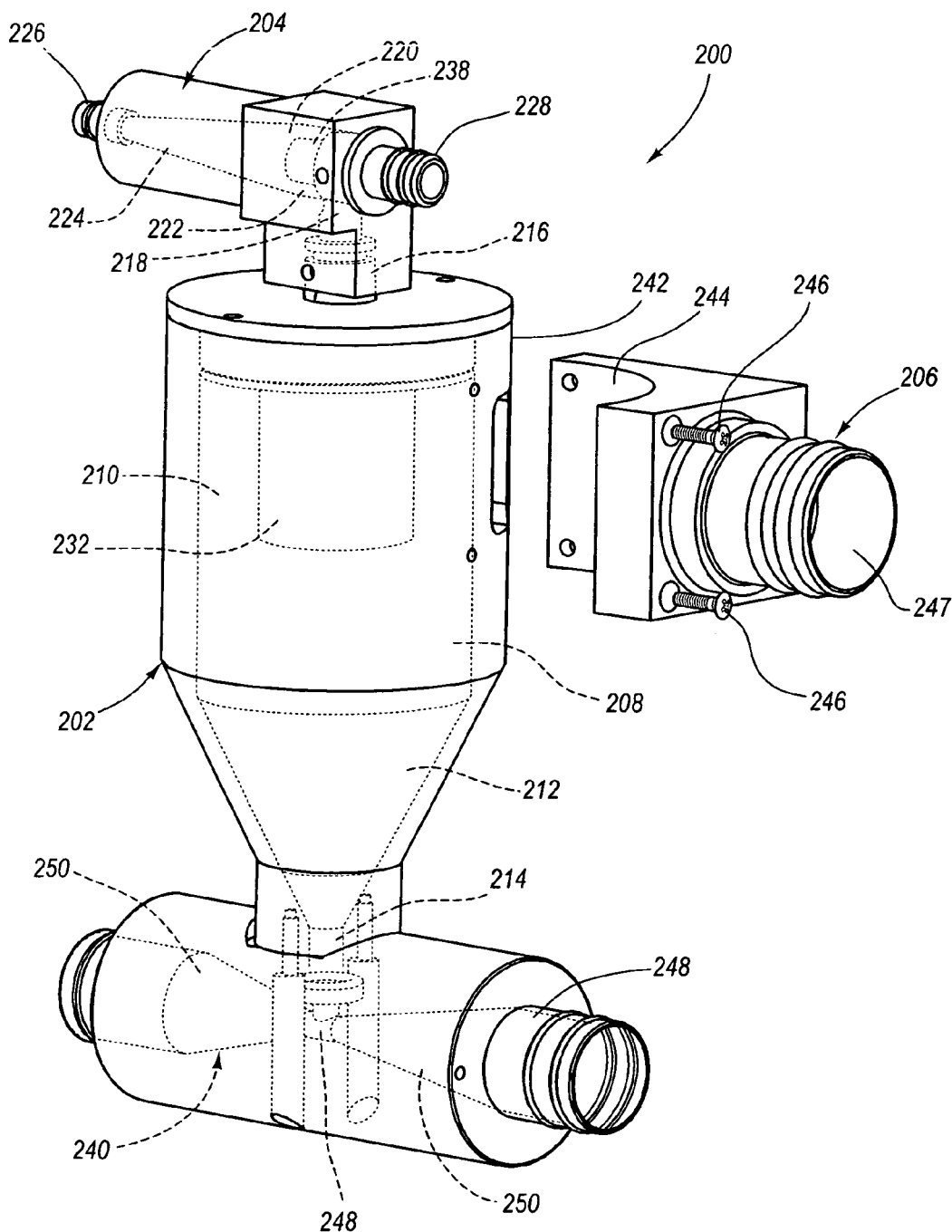
FIG. 3 is an exploded perspective view of another embodiment of a particle separation apparatus coupled to a venturi tube.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the invention, as claimed, but is merely representative of the embodiments of the invention. While the various aspects of the embodiments are presented in drawings, the drawings are not necessarily drawn to scale unless specifically indicated.

For this application, the phrases "connected to," "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. The term "abut" or "abutting" refers to items that are in direct physical contact with each other, although the items may not necessarily be attached together.

FIG. 1 represents one embodiment of a particle separation apparatus 100 as shown from a perspective view. The particle separation apparatus 100 includes a first vortex separator 102 coupled to a second vortex separator 104. The first vortex separator 102 may be a classical vortex separator, also known as a cyclone separator. However, alternative vortex designs may be used that are not considered "classical." For example, alternative vortex separator designs may be used that operate on the same or similar principles as classical vortex devices.

According to the embodiment shown in FIG. 1, the first vortex separator 102 includes a sample inlet 106 which receives the particle-laden air sample to be analyzed. The sample inlet 106 may be separably attachable to a vortex chamber 108. Allowing the inlet 106 to be removable from the chamber 108 may help reduce costs associated with manufacturing parts. For example, the particle separation apparatus 100 may be manufactured by machining or through an injection mold process. Allowing the inlet 106 and the chamber 108 to be manufactured separately, may make the injection molding process more feasible, and hence reduce the costs associated with manufacture. Alternatively, the inlet 106 could be integrated with the chamber 108.

The inlet 106 introduces the sample air stream into the chamber 108 tangentially. This manner of introduction, coupled with the shape of the vortex chamber 108 causes the particle-laden air sample to spiral within the chamber 108 creating centrifugal forces therein. However, alternative inlet 106 configurations may be used, such as an axial inlet instead of a tangential inlet. An axial inlet would introduce the sample air stream along or substantially parallel with the longitudinal axis of the first vortex chamber 108.

The vortex chamber 108 may include a cylindrical portion 110 and a conical portion 112. The inlet 106 may be coupled to the cylindrical portion 110 of the chamber 108. As the particle-laden air sample spirals downward within the cylindrical portion 110 of the chamber 108, larger particles are forced toward the sides of the chamber 108. Smaller particles, along with a majority of the air stream, may be drawn into the upwardly-spiraling inner vortex. The larger particles, however, are not usually drawn into the inner vortex and are typically left outside the main air stream and travel to a large particle outlet 114.

The large particle outlet 114 may be a minor flow outlet 114. Alternatively, the large particle outlet 114 may be coupled to a particle collection chamber. The large particle outlet 114 may be an axial discharge along the longitudinal axis of the vortex chamber 108. The large particle outlet 114 may be part of the exhaust flow, containing particles not within a desired size range of particles. For example, the first vortex separator 102 may be designed to separate particles that are too big to be respirable from particles that are small enough to be respirable. For instance, it may tend to separate particles that are smaller than about 10 microns in diameter (by sending those particles through the small particle outlet 116) from those greater than 10 microns (by sending those particles through the large particle outlet 114).

This does not necessarily mean that all particles larger than the desired size are separated from those that are smaller, since it is likely that some larger particles may be included in the small particle stream and some smaller particles may be included in the large particle stream. For example, a vortex separator designed to separate particles at about 10 microns will tend to separate particles larger than 10 microns from those smaller than 10 microns, but the separation will likely not be perfectly efficient. Moreover, some particles may adhere to the walls of the vortex separator 102, 104 or to conduits in the device. The efficiency of the separation depends on many factors other than the physical design of the vortex separator 102, 104, such as particle size, particle size distribution, pressure, static electricity, and wetness.

The air sample flow containing particles smaller than the desired size, which is typically the major air flow, may be delivered to a small particle outlet 116 on a top portion of the vortex chamber 108. The small particle outlet 116 may be a major flow outlet 116. The major flow or small particle outlet 116 may be coupled to an inlet 118 of the second vortex separator 104. The inlet 118 of the second vortex separator 104 may be similar to the inlet 106 of the first vortex separator 102, in that it introduces the sample air stream tangentially into a vortex chamber 120 of the second vortex separator 104. The inlet 118 of the second vortex separator 104 may also be separably attachable.

The vortex chamber 120 of the second vortex separator 104 has a cylindrical portion 122 and a conical portion 124. The larger particles within the air sample introduced into the second vortex separator 104 are forced to the sides of the chamber 120 and are channeled out of the minor flow outlet 126. The remaining air stream having particles smaller than the desired size is discharged out of the major flow outlet 128. Both the minor and major flow outlets 126, 128 discharge from the vortex chamber 120 axially. The major flow outlet 128 of the second vortex separator 104 is a part of the exhaust flow, containing particles not within the desired size range of particles.

The particles that are channeled out of the minor flow outlet 126 of the second vortex separator 104 are particles that are within the desirable size range. For example, the first vortex separator 102 may have separated out of the sample particles larger than about 10 microns in diameter, while the second vortex separator 104 may have separated out those particles larger than 1 micron in diameter. However, particles within the desirable size range may include a trace amount of particles outside of the size range.

Consequently, the resultant major flow stream of the second vortex separator 104 contains most of the air flow, but also particles that are smaller than 1 micron, while the minor flow stream contains a concentrated amount of particles having a range of sizes between about 1 micron in diameter and about 10 microns in diameter. This concentrated flow of particles is delivered from the minor flow outlet 126 to the particle detection system for analysis. Delivery to the particle detection system may be direct, or indirect, where there is an intervening component between the minor flow outlet 126 and the particle detection system.

FIG. 2A illustrates the particle separation apparatus 100 of FIG. 1 as shown from a side elevation view. This view is shown looking into the sample inlet 106 of the first vortex separator 102 and the major flow outlet 128 of the second vortex separator 104. The particle separation apparatus 100 is sectioned along the plane 2B-2B, which passes through the longitudinal axis of both the first 102 and second 104 vortex separators.

FIG. 2B represents the particle separation apparatus 100 of FIG. 2A from a side cross sectional view, as viewed along the cross-sectional plane 2B-2B. A particle-laden air stream is introduced to the particle separation apparatus 100 via the sample inlet 106 of the first vortex separator 102. The sample inlet 106 delivers the air stream into the cylindrical portion 110 of the vortex chamber 108 tangentially. The air stream spirals around the cylindrical portion 110 proceeding downward toward the axial large particle outlet 114, which may be the minor flow outlet 114.

As the air stream spirals, centrifugal forces push the larger particles toward the chamber wall 130. The air stream proceeds down the cylindrical portion 110 of the chamber. As the diameter of the chamber 108 decreases in the conical portion 112, so does the diameter of the spiraling air stream until its diameter is roughly equivalent to the diameter of a vortex finder 132. A majority of the air stream is caught up in the inner vortex, spiraling axially upward within the chamber 108 toward the vortex finder 132. The vortex finder 132 may be located in the center of the chamber 108 to receive the upward spiraling vortex. The vortex finder 132 may be in fluid communication with the small particle outlet 116, or in the present embodiment, the major flow outlet 116 where the air stream exits the first vortex separator 102.

Typically, the larger particles that were forced to the chamber wall 130 do not exit the first vortex separator 102 via the vortex finder 132, but rather flow downward to the apex 134 of the conical portion 112 and are discharged out of the minor flow outlet 114. Consequently, the first vortex separator 102 is designed as a scalper.

The dimensions of the first vortex separator 102, e.g., the cross sectional areas and lengths of flow channels as well as the inlet flow rate help determine the size of the particles that are separated. In biological particle detection, particles within a respirable range are often targeted. The range of particle sizes that are sometimes described as respirable may be within the range from 1 to 10 microns. However, the range may have a different lower diameter, such as 0.5 microns and/or a different upper diameter, such as 20 microns. Accordingly, the embodiment described and illustrated in FIG. 2B may have a first vortex separator 102 designed to separate particles at about 10 microns, and particles larger than 10 microns are discharged axially through the minor flow outlet 114.

The first vortex separator 102 may be a classical vortex separator, in that it has a tangential inlet and axial discharge. However, as would be apparent to one having skill in the art, alternative configurations are envisioned. These configurations could include, for instance, any number of different combinations of axial, peripheral, or tangential inlets or outlets. For example, a vortex separator having a tangential inlet and peripheral discharge could be used. Alternatively, a vortex separator having an axial inlet and axial discharge could be employed. Further still, a vortex separator having an axial inlet and peripheral discharge may also be used.

Referring still to FIG. 2B, the air stream sample having particles smaller than about 10 microns may flow out the small particle or major flow outlet 116 of the first vortex separator 102 into the inlet 118 of the second vortex separator 104. The inlet 118 may be coupled to the second vortex separator 104 in such a way that the air sample is introduced into the vortex chamber 120 tangentially. The air stream then spirals around the cylindrical portion 122 of the chamber 120, creating a centrifugal force that pushes larger particles toward a chamber wall 136. When the spiraling air stream is drawn into the vortex finder 138, it spins in a vortex axially upward, leaving behind the larger particles to exit the minor flow outlet 126.

The second vortex separator 104 may tend to separate particles at about 1 micron. Consequently, the second vortex separator 104 may also function as a scalper. In addition to functioning as a scalper, the second vortex separator 104 may also function as a concentrator of particles that are within a desirable size range. For example, according to the embodiment of FIG. 2B, particles that are between about 1 micron to about 10 microns in diameter exit the particle separation apparatus 100 at the minor flow outlet 126. At this point the particles within the desirable size range are not in the air stream major flow. The number of particles within the target size range has increased per unit volume. This concentration increase may be by a factor of at least 2:1. In one embodiment the increase of target particle concentration is by a factor of about 10:1, because the target particles are concentrated in a volume approximately 10 times less than that of the first-stage inlet 106 volume. The concentrated particle air stream containing the target range of particle sizes are then delivered to a particle detection system (not shown).

The majority of the air stream flow which contains particles that are smaller in size, for example, smaller than about 1 micron in diameter, are received by a vortex finder 138 located centrally in the chamber 120. The vortex finder 138 is in fluid communication with the major flow outlet 128. According to one embodiment, the major flow outlet 128 is a part of the exhaust flow, containing particles outside of the target particle size.

In alternative embodiments, additional stage vortex separators and/or concentrators or other scalpers may be used to further separate and/or concentrate the sample to better increase the performance of the particle detector. For example, in some applications, additional stage vortex separators may be used to further target a particular particle size range and decrease the flow rate (and increase concentration) of those particles. This may increase the amount of time the particles are in the view volume of a LIF particle sensor system, which may increase sensor performance.

FIG. 3 represents another embodiment of a particle separation apparatus 200 coupled to a venturi tube 240 as shown from an exploded perspective view. The outline of many components internal to a housing 242 of the particle separation apparatus 200 are shown in phantom. The particle separation apparatus 200 includes a first vortex separator 202 and a second vortex separator 204. The first vortex separator 202 includes a tangential sample inlet 206, an axial minor flow outlet 214, an axial major flow outlet 216, and a vortex chamber 208 having a cylindrical portion 210, a conical portion 212 and a vortex finder 232. The second vortex separator 204 also has a tangential inlet 218, an axial minor flow outlet 226, an axial major flow outlet 228, and a vortex chamber 220 having a cylindrical portion 222, a conical portion 224 and a vortex finder 238.

The sample inlet 206 of the first vortex separator 202 may be separably attachable to the housing 242 of the first vortex chamber 208, allowing it to be removed and reattached when necessary. The inlet 206 may have a concave surface 244 contoured to the shape of the chamber housing 242. The concave surface 244 may be configured to firmly abut the housing 242 and then attach thereto through the use of removable fasteners 246.

Since the inlet 206 is typically connected to tubing, the inlet 206 may be round at one end opening 247. The other end opening (not shown) may be rectangular in cross section to shape the tangential inlet flow into the vortex chamber 208. The surface around the opening 247 may be barbed to facilitate attachment to tubing. Furthermore, the outlets 226, 228 of the second stage vortex separator 204 may also be barbed for attachment to tubing.

The two-stage vortex particle separation device 200 separates out particles within a desirable size range according to the principles described in conjunction with the embodiments shown in FIGS. 1 through 2B. However, according to this embodiment, a venturi tube 240 may be coupled to the minor flow outlet 214 of the first vortex separator 202 to draw large particles out of the vortex chamber 208.

The venturi tube 240 may be a constriction within a flow line 248 that causes a drop in pressure as the exhaust flow travels through it, according to Bernoulli's principle. The venturi tube 240 may have a narrow throat 248 between two tapered sections 250. The drop in pressure creates a pressure differential that may draw the exhaust flow exiting the minor flow outlet 214 of the first vortex separator 202.

Alternative eductor devices, other than a venturi tube 240 may be used, which are passive devices to create a pressure differential or vacuum to draw the exhaust flow out of the minor flow outlet 214 of the first vortex separator 202. Active devices, such as a pump may also be employed to create a pressure differential to draw or push the exhaust flow out of the minor flow outlet 214 of the first vortex separator 202.

When the particle separation apparatus 200 is used in a dirty environment, such as in a ventilation system at airports or subway terminals, large fibrous particles that may be long and narrow, which originate from clothing and the like may clog the minor flow outlet 214. Particles may tend to clog the minor flow outlet 214 for other reasons, such as wetness or static electricity. The vacuum created by the venturi tube 240 in communication with the minor flow outlet 214 helps to mitigate this concern. The use of a vortex separator with an eductor helps prevent the clogging concerns prevalent when using alternative scalping devices, such as virtual impactors.

The housing 242 of the particle separation apparatus 200 of FIG. 3 may be constructed of metal, such as aluminum 6061-T6. A grounded metal housing 242 may limit static charge that could develop on the apparatus 200, which may cause some particles to stick to the interior of the vortex chambers 208, 220. With a metal construction the apparatus 200 may be cast from one piece, or alternatively, may consist of two halves for machining. Furthermore, the housing 242 may alternatively be constructed of plastic or a conductive plastic or similar material, allowing for an injection molded manufacture.

Figure 4B:
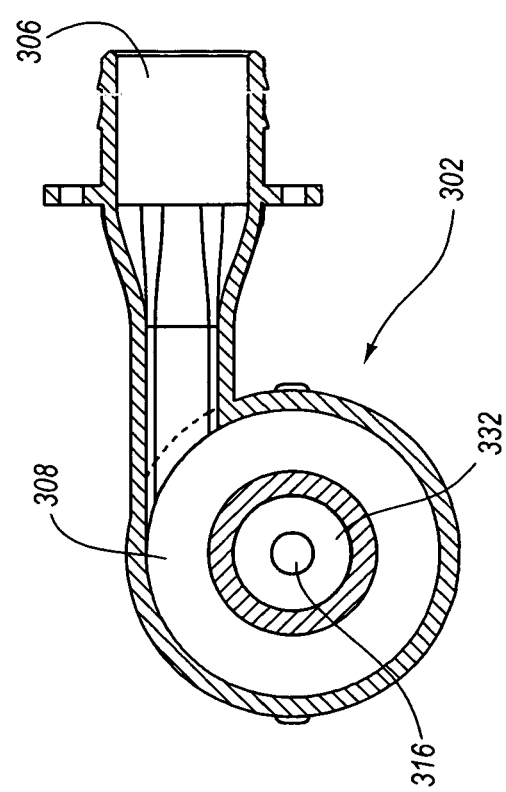
FIG. 4B is a cross sectional plan view of the first stage vortex separator of FIG. 4A as viewed along the cross-sectional plane 4B-4B.
Figure 4A:
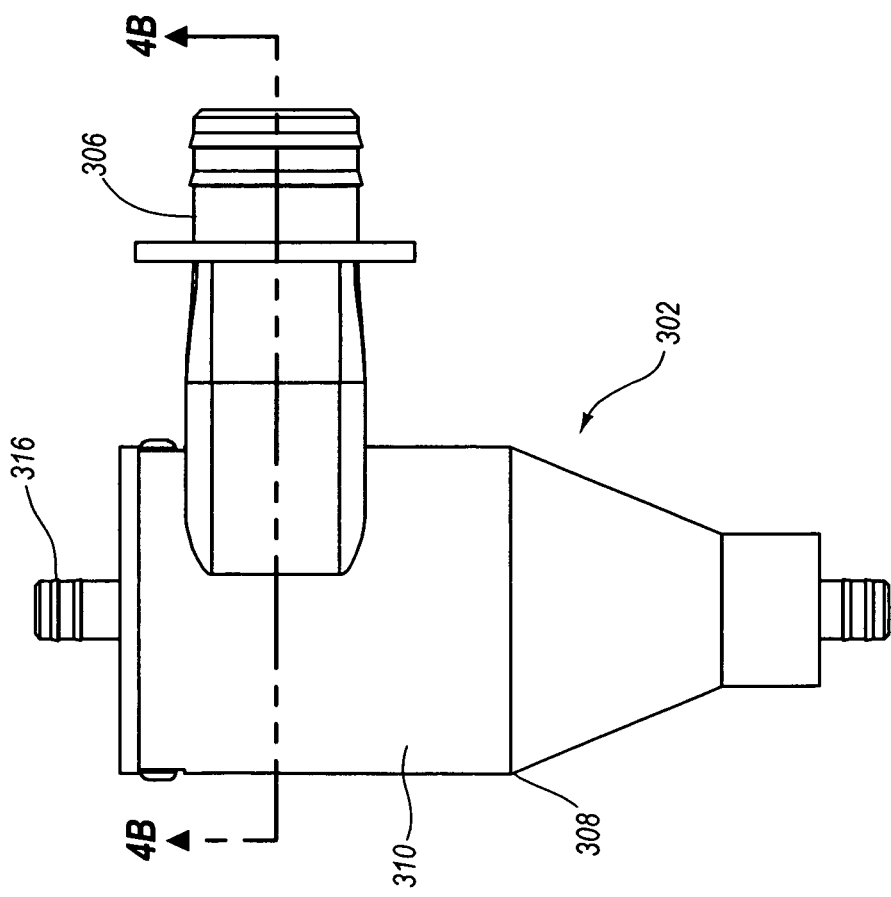
FIG. 4A is a side elevation view of a first stage vortex separator that is a particle separation apparatus.

FIG. 4A represents a first stage vortex separator 302 that is part of a particle separation apparatus as shown from a side elevation view. Plane 4B-4B extends through a sample inlet 306 and a cylindrical portion 310 of a vortex chamber 308. Referring to FIG. 4B, the first stage vortex separator 302 of FIG. 4A is viewed from a cross sectional plan view along the plane 4B-4B. FIG. 4B is looking upward, into the vortex chamber 308 towards a major flow outlet 316.

A particle-laden sample air stream enters the first stage vortex separator 302 through the sample inlet 306. The air stream enters the vortex chamber 308 tangentially and spirals down the chamber 308, separating out large particles, such as those larger than about 10 microns, through centrifugal forces. The upward-spiraling inner vortex is received by a vortex finder 332 which may be coupled to the major flow outlet 316. The major flow outlet 316 may lead the sample air stream into the second stage vortex separator.

FIG. 5A represents a second stage vortex separator 404 that is part of a particle separation apparatus as shown from a side elevation view. Plane 5B-5B extends through an inlet 418 and a vortex chamber 420. Referring to FIG. 5B, the second stage vortex separator 404 of FIG. 5A is shown from a cross sectional plan view along the plane 5B-5B. FIG. 5B is looking upward in the vortex separator 404 toward a major flow outlet 428.

The air sample that exited the major flow outlet of the first vortex separator is delivered to the inlet 418 of the second stage vortex separator 404. The air stream enters the vortex chamber 420 tangentially. As the air stream spirals down the chamber 420, centrifugal forces separate out relatively large particles, such as those between 10 microns and 1 micron. The air sample containing particles smaller than about 1 micron is caught up in the upwardly-spiraling inner vortex. The inner vortex is received by a vortex finder 438, leaving particles between 1 and 10 microns in the vortex chamber 420. The vortex finder 438 is in communication with the major flow outlet 428, which may contribute to the exhaust flow.

Figure 6:
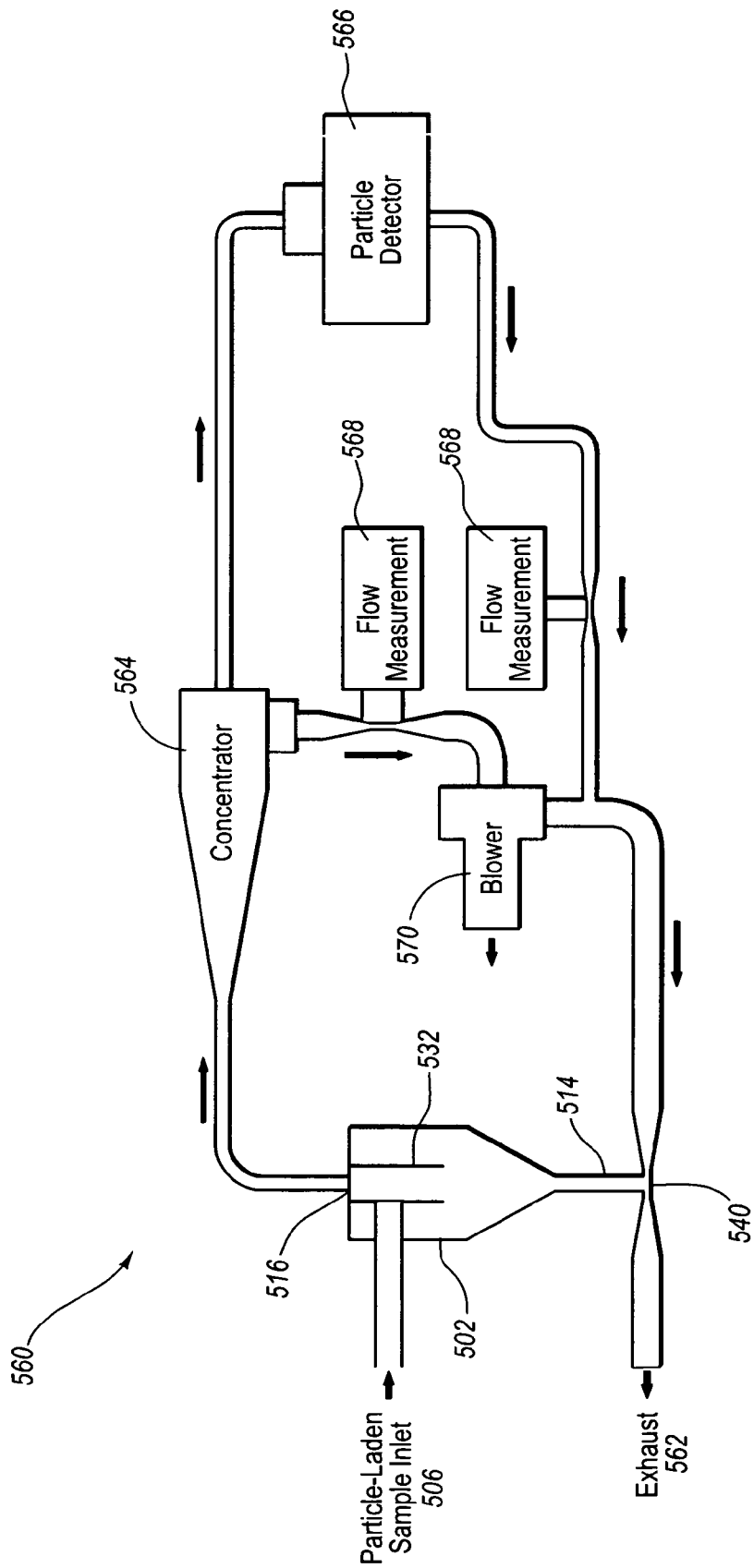
FIG. 6 is a block diagram of a flow system of a particle separation apparatus and particle detector in a particle detection system.
Figure 7:
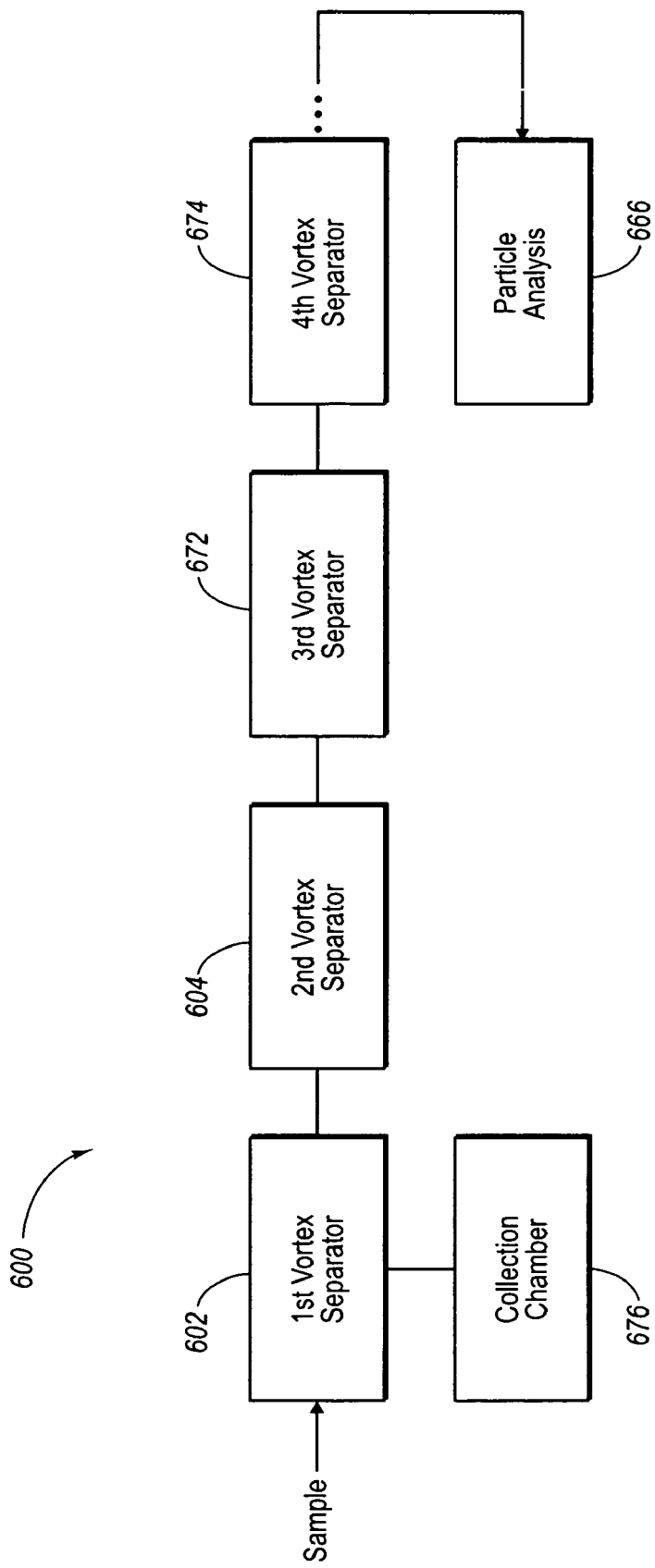
FIG. 7 is a block diagram of another alternative embodiment of a particle separation apparatus.

FIG. 6 is a block diagram of a flow system 560 of a particle separation and detection system, according to one embodiment. A particle-laden air sample is introduced to the flow system 560 through a sample inlet 506. The air sample enters a first vortex separator 502 where larger particles, such as those larger than 10 microns in diameter, are separated out of the air stream according to the principles discussed in conjunction with the preceding Figures. The large particles exit the first vortex separator 502 through a minor flow outlet 514, which optionally may be coupled to an eductor such as a venturi tube 540. The venturi tube 540 carries the exhaust flow 562, and creates a vacuum at the minor flow outlet 514 to draw the large particles separated out from the air stream into the exhaust flow 562.

The sample air stream is received by a vortex finder 532 which may be coupled to a major flow outlet 516. The major flow outlet 516 is in fluid communication with a concentrator device 564. The concentrator device is configured to increase a concentration of particles within a desirable size range in preparation for delivery to a particle detector or particle analyzer 566. The concentrator device 564 may also be a scalper for removing particles that are outside of the target particle size range. The concentrator device 564 may be a virtual impactor or similar device used to separate particles by size into two airstreams. The air stream containing the target particle size is delivered to the particle detector or air stream analyzer 566 for analysis. Alternatively, the concentrator device 564 could be a second stage vortex separator, as described herein.

The air stream containing particles outside of the target particle size range is discharged into the exhaust flow 562. The exhaust flow 562 may optionally encounter a flow measurement device 568, and a concentrator blower 570. The concentrator blower 570 may have a blower bypass flow for cooling bearings. The exhaust flow 562 eventually is channeled to outside the flow system 560.

The concentrated air stream containing particles within the desirable size range are delivered to the particle detector 566. The particle detector 566 may be an optical particle detector, such as a laser-induced fluorescence detection system or an LED-based detection system. However, alternative particle detection systems may be used as known to those having skill in the art. For example, the concentrated particle stream may be delivered to a particle counter, particle analyzer, or other device that analyzes the particle-laden air stream through optical, chemical, or other analytical techniques. For example, the particle-laden air stream may be interrogated through Raman spectroscopy, mass spectrometry or alternative techniques, if desired. The concentrated particle air stream may then be included in the exhaust air flow 562 after analysis.

These and other vortexes and other concentrators and/or separators operating on the same principles can be usefully employed as a front end, or within, a variety of particle detection and analysis systems. These could include systems sold or developed by Hach Ultra Analytics Homeland Security Technologies, such as the Bioni and BioLert. These could include versions of the: Fluorescent Aerodynamic Particle Sizer (FLAPS) developed by the Canadian Ministry of National Defense; APS (Aerodynamic Particle Sizer) sold by TSI, Inc., including the UV-APS; the Single-Particle Fluorescence Counter (SPFC), developed by the Naval Research Laboratory (NRL); PS-BARTS sold by General Dynamics of Canada; Fluorescence Particle Counter (FPC) or Aerosol Fluorescence Spectrum Analyzer (AFSA) developed by the U.S. Army Research Laboratory. These types of systems can employ lasers (such as laser diodes) or other sources of electromagnetic radiation to illuminate an air stream or particles; lasers (such as laser diodes) or light sources at single or multiple wavelengths to induce fluorescence in particles; one or more detectors to detect electromagnetic radiation scattered, reflected, transmitted, or emitted in response to the sources of electromagnetic radiation; hardware or software to size or classify particles, to control the system (such as activating one or more lasers only when certain size particles are optically detected); and hardware or software to send an alarm or signal when potential threat particles are detected. For instance, the BioLert 2×16C5+1 (as disclosed in "Multispectral-diode-laser-induced fluorescence biological particle sensor," Geoffrey A. Wilson and Richard K. DeFreez, Proc. SPIE Int. Soc. Opt. Eng. 5617, 46 (2004)) was designed to use two diode lasers at different wavelengths, detection of sixteen fluorescence emission bands bundled into five user-defined linear combinations, an elastic scatter detector using simultaneous excitation and detection at multiple wavelengths, and a highly integrated air sampling system, including a scalper designed to remove large (approximately >10 micron diameter) particles in its minor exhaust, and a concentrator to remove most of the air and small particles (approximately <0.5 micron diameter); leaving intermediate-size ("respirable range") particles concentrated by about 10:1 relative to the atmosphere. The vortexes and other separators and concentrators disclosed elsewhere in this application could be used instead of that integrated air sampling system.

The particle detector 566 and flow system 560, including the first vortex separator 502 and concentrator device 564 may all be included in a single housing of a particle detection system, which may be coupled to or within an air duct system in postal handling, airport terminal, or similar environment.

FIG. 7 is a block diagram of another alternative embodiment of a particle separation apparatus 600. The particle separation apparatus 600 may be a multi-stage system including multiple stage scalpers and concentrators. According to the embodiment depicted, a first vortex separator 602 may be coupled to a second vortex separator 604. Furthermore, a third and fourth stage vortex separator 672, 674 may also be used to further select a particular particle size range or further concentrate the particle-laden air sample by increasing the amount of particles of interest per unit volume. Each vortex separator 602, 604, 672, 674 may be in communication with a flow system as described in conjunction with FIG. 6. Alternatively, the vortex separators may be coupled to a particle collection chamber 676 for collecting particles for analysis or to be discarded.

In alternative embodiments, additional stage vortex separators and/or concentrators or other scalpers may be used to further separate and/or concentrate the sample to better increase the performance of the particle detector. For example, one system may include two scalpers and a concentrator device. Another alternative may have one scalper and two concentrators. Furthermore, two scalpers and two concentrators may also be used. The various arrangements and types of scalpers and concentrators would be apparent to those having skill in the art.

Once the sample air stream has passed through the particle separation apparatus 600, it may then be provided to a particle analyzer 666. As discussed above, multiple methods of particle analysis may be used, such as LIF detection, particle size analysis, particle counting, and Raman spectroscopy. The fourth stage vortex concentrator 674 may also concentrate the particle stream for deposition onto a substrate or otherwise pass the particles on for further analysis, such as flow cytometry, immunoassay, and nucleic acid amplification (such as PCR).

While specific embodiments and applications have been illustrated and described, it is to be understood that the invention is not limited to the precise configuration and components disclosed herein. Various modifications, changes, and variations which will be apparent to those skilled in the art may be made in the arrangement, operation, and details of the methods and systems disclosed herein without departing from the spirit and scope of the invention.

What is claimed is:

1. An apparatus for the separation and detection of particles, comprising:

a first vortex separator;

a second vortex separator in communication with the first vortex separator; and an optical particle detector in communication with the second vortex separator;

such that the first and second vortex separators, collectively, are configured to provide particles that are within a desirable size range to the optical particle detector.

2. The apparatus of claim 1, wherein the first and second vortex separators each include a sample inlet, a small particle outlet, a large particle outlet, and a vortex chamber.

3. The apparatus of claim 2, wherein at least one of the large particle outlets of the first and second vortex separators is coupled to a particle collection chamber.

4. The apparatus of claim 2, wherein each large particle outlet is a minor flow outlet and each small particle outlet is a major flow outlet.

5. The apparatus of claim 4, wherein the major flow outlet of the first vortex separator is coupled to the inlet of the second vortex separator and the minor flow outlet of the second vortex separator is configured to contain a flow of particles within the desirable size range.

6. The apparatus of claim 5, wherein the minor flow outlet of the first vortex separator and the major flow outlet of the second vortex separator are part of an exhaust flow of the particle separation apparatus, the exhaust flow configured to contain particles that are outside of the desirable size range.

7. The apparatus of claim 2, wherein the inlets of the first and second vortex separators are arranged such that sample flows from each inlet into the respective vortex chamber tangentially.

8. The apparatus of claim 7, wherein at least one of the inlets of the first and second vortex separators is separably attachable to its respective vortex chamber through removable fasteners.

9. The apparatus of claim 1, wherein the desirable size range is a range from about 1 micron in diameter to about 10 microns in diameter.

10. The apparatus of claim 1, wherein the second vortex separator further increases a concentration of particles that are within the desirable size range.

11. The apparatus of claim 10, wherein the second vortex separator increases the concentration of particles within the desirable size range by at least a factor of 2:1.

12. The apparatus of claim 1, wherein the optical particle detector is a laser-induced fluorescence sensor.

13. The apparatus of claim 4, wherein the minor flow outlet of the first vortex separator is coupled to an eductor for drawing exhaust out of the minor flow outlet.

14. The apparatus of claim 13, wherein the eductor is a venturi tube.

15. The apparatus of claim 13, wherein a minor flow of the minor flow outlet is produced by a pump.

16. The apparatus of claim 1, further comprising a third vortex separator in communication with the second vortex separator, such that the first, second and third vortex separators in combination are in communication with the optical particle detector and are configured to select and concentrate particles that are within the desirable size range.

17. The apparatus of claim 16, further comprising a fourth vortex separator in communication with the third vortex separator, such that the first, second, third and fourth vortex separators, in combination, are in communication with the optical particle detector and are configured to concentrate particles that are within the desirable size range.

18. A particle separation apparatus, comprising:
a first vortex separator, including:
an inlet configured to receive a particle-containing sample;
a small particle outlet;
a large particle outlet;
a vortex chamber; and
a concentrator device in communication with the first vortex separator, the concentrator device comprising a second vortex separator and configured to increase a concentration of particles within the sample; and
an eductor coupled to the large particle outlet of the first vortex separator for drawing exhaust out of the large particle outlet;
wherein the first vortex separator and the concentrator device in combination are adapted to substantially separate out particles from the sample that are outside a desirable size range and increase the concentration of particles that are within the desirable size range for delivery to a particle detector.

19. The particle separation apparatus of claim 18, wherein the large particle outlet is a minor flow outlet and the small particle outlet is a major flow outlet.

20. The particle separation apparatus of claim 19, wherein the second vortex separator comprises an inlet coupled to the major flow outlet of the first vortex separator.

21. The particle separation apparatus of claim 20, wherein the second vortex separator has a major flow outlet and a minor flow outlet, such that the particles within the desirable size range are delivered from the minor flow outlet to the particle detector.

22. The particle separation apparatus of claim 18, wherein the first vortex separator substantially separates out particles from the sample that are larger than about 10 microns in diameter, and the second vortex separator substantially separates out particles from the sample that are smaller than about 1 micron in diameter.

23. The particle separation apparatus of claim 21, wherein the eductor is a venturi tube.

24. The particle separation apparatus of claim 19, wherein a minor flow of the minor flow outlet is produced by a pump.

25. A particle separation apparatus, comprising:

a first vortex separator, including a sample inlet, a major flow outlet, a minor flow outlet, and a vortex chamber, the first vortex separator separating out particles from a sample that are larger than a maximum size limit;

a second vortex separator, including an inlet, a major flow outlet, a minor flow outlet and a vortex chamber, the second vortex separator separating out particles from the sample that are smaller than a minimum size limit and further increasing the concentration of particles that are within a range between the maximum size limit and the minimum size limit;

a third vortex separator in communication with the second vortex separator, such that the first, second and third vortex separators, in combination, are in communication with a particle detection system and are configured to select and concentrate particles that are within the size range.

* * * * *

UNITED STATES PATENT AND TRADEMARK OFFICE
CERTIFICATE OF CORRECTION

PATENT NO. : 7,390,339 B2
APPLICATION NO. : 11/122408
DATED : June 24, 2008
INVENTOR(S) : Bret R. Warrick, Ivan K. Horban and Michael M. Carrabba It is certified that error appears in the above-identified patent and that said Letters Patent is hereby corrected as shown below:

Column 2, Line 32 reads, "...the invention's the embodiments will be described..." which should read, "...the invention's scope, the embodiments will be described..."

Column 2, Line 33 reads, "...specificity and detail use of the accompanying..." which should read, "...specificity and detail through use of the accompanying..."

Signed and Sealed this

Twenty-second Day of September, 2009

David J. Kappos
*Director of the United States Patent and Trademark Office*